(12) United States Patent
Lomax

(10) Patent No.: US 10,451,516 B2
(45) Date of Patent: Oct. 22, 2019

(54) SEALED BLADDER ASSEMBLY AND METHOD

(71) Applicant: The Boeing Company, Chicago, IL (US)

(72) Inventor: Michael E. Lomax, Woodinville, WA (US)

(73) Assignee: The Boeing Company, Chicago, IL (US)

(*) Notice: Subject to any disclaimer, the term of this patent is extended or adjusted under 35 U.S.C. 154(b) by 142 days.

(21) Appl. No.: 15/678,330

(22) Filed: Aug. 16, 2017

(65) Prior Publication Data

US 2017/0343447 A1    Nov. 30, 2017

Related U.S. Application Data

(62) Division of application No. 13/928,569, filed on Jun. 27, 2013, now Pat. No. 9,772,253.

(51) Int. Cl.
    *G01M 3/28* (2006.01)
    *G01M 5/00* (2006.01)
    *G01N 3/12* (2006.01)

(52) U.S. Cl.
    CPC ........ *G01M 3/2846* (2013.01); *G01M 5/0025* (2013.01); *G01M 5/0075* (2013.01); *G01N 3/12* (2013.01); *Y10T 29/49826* (2015.01)

(58) Field of Classification Search
    CPC ............. G01M 3/2846; G01M 5/0025; G01M 5/0075; G01N 3/12; Y10T 29/49826
    USPC ....................... 138/30, 89–94, 109
    See application file for complete search history.

(56) References Cited

U.S. PATENT DOCUMENTS 6,053,210 A * 4/2000 Chapman .................. F16K 7/10
                                                         138/46
6,962,165 B2 * 11/2005 Delprat ................... F16K 17/34
                                                        137/498

* cited by examiner

*Primary Examiner* — Bayan Salone
(74) *Attorney, Agent, or Firm* — Walters & Wasylyna LLC

(57) ABSTRACT

A bladder assembly including a body, a bladder received in the body, the bladder defining an internal volume and including an annular sealing bead, the sealing bead defining an opening into the internal volume, and a sealing member including a shaft having a first end and a second end, and an engagement portion connected proximate the second end, the sealing member being partially received within the internal volume and being moveable between at least a first position, wherein the engagement portion is spaced from the sealing bead, and a second position, wherein the sealing bead is compressed between the engagement portion and the body.

20 Claims, 9 Drawing Sheets

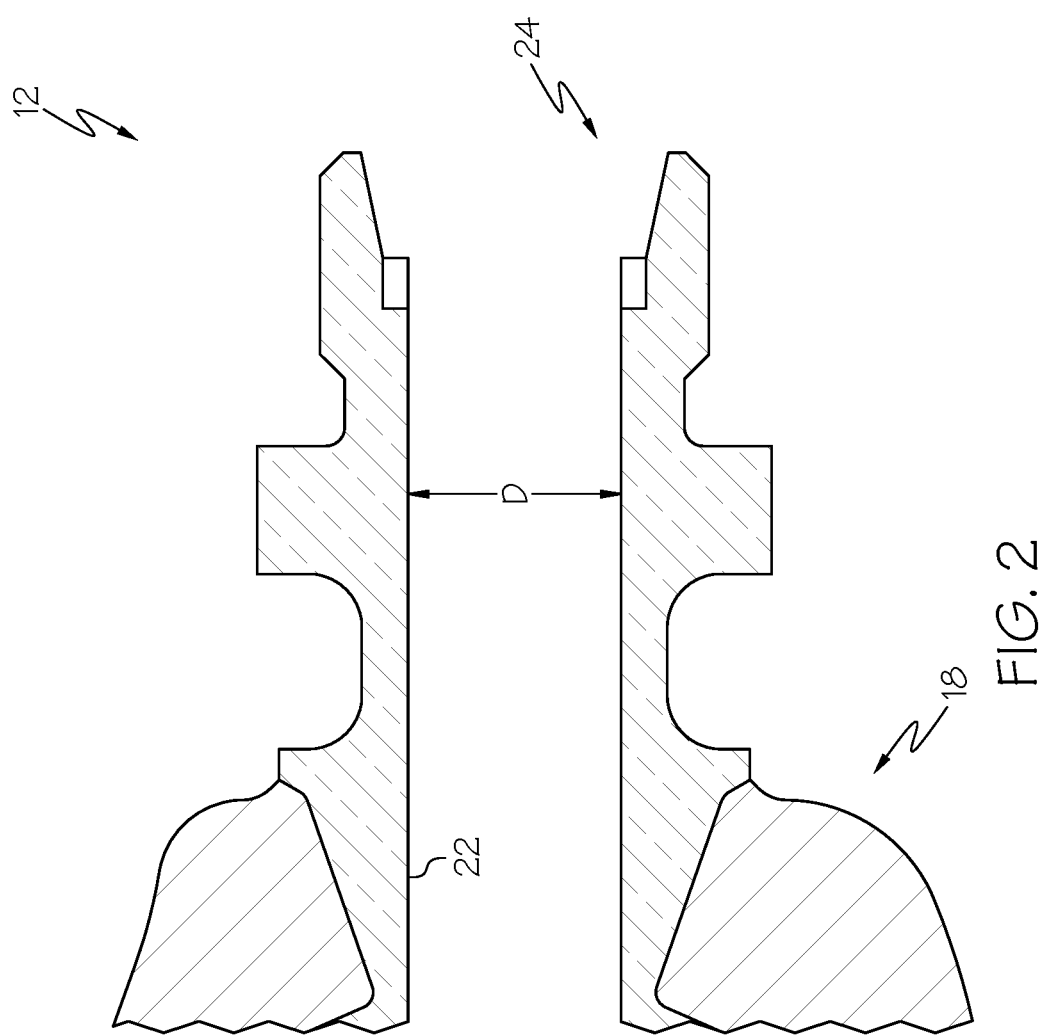

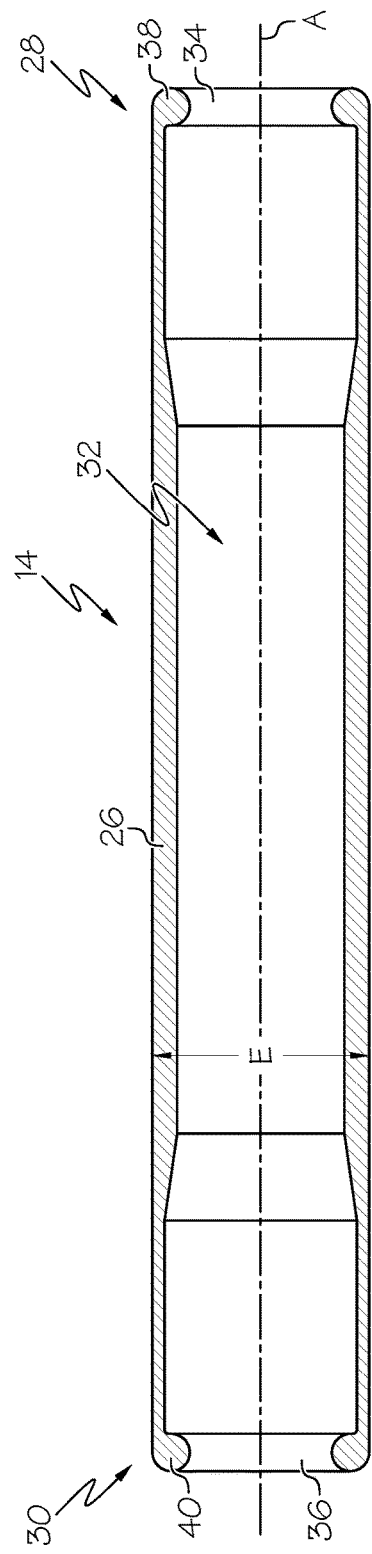
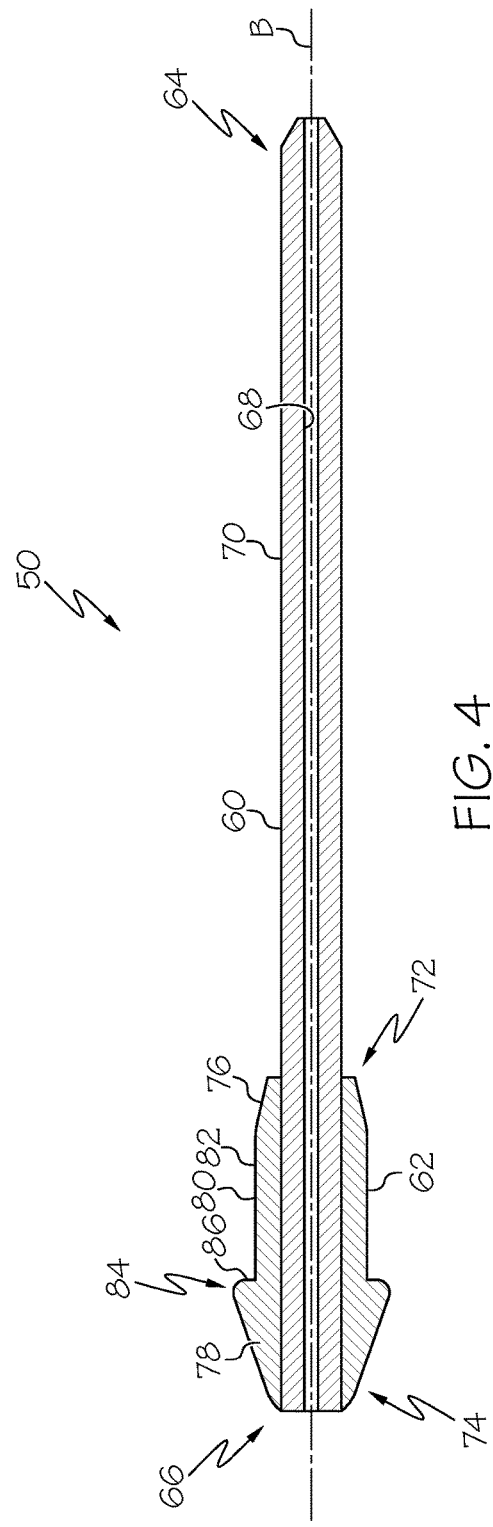

SEALED BLADDER ASSEMBLY AND METHOD

PRIORITY

This application is a divisional of U.S. Ser. No. 13/928,569 filed on Jun. 27, 2013.

FIELD

This application relates to bladder sealing and, more particularly, to apparatus and methods for sealing a bladder for pressure testing.

BACKGROUND

Various parts, such as composite parts, are subjected to high pressures while in use. Therefore, during the research and development phase, such parts are vigorously tested to ensure they are capable of withstanding high pressures for prolonged periods of time. Indeed, parts are often tested at pressures that are significantly higher than the pressures at which the parts were design to operate.

Pressure testing, particularly high pressure testing, typically involves introducing a pressurized fluid, such as a gas or hydraulic fluid, to act on the part under test. Depending on the structure and composition of the part, it may be difficult to maintain the pressures required to run the test to completion. For example, parts with holes and/or parts constructed from porous materials may be difficult to subject to high pressures.

Thus, bladders have been used in pressure testing. For example, a bladder may be inserted into a bore within the part under test and then the bladder may be pressurized. The bladder contains the pressurized fluid, thereby facilitating pressure testing of various parts, including parts with holes.

Unfortunately, using bladders for pressure testing introduces an additional step, which often complicates the test and increases costs. For example, it often becomes quite difficult to obtain a proper, pressure-tight seal in the bladder, particularly when the bladder is being used for high pressure testing.

Accordingly, those skilled in the art continue with research and development efforts in the field of pressure testing.

SUMMARY

In one embodiment, the disclosed bladder assembly may include a body, a bladder received in the body, the bladder defining an internal volume and including an annular sealing bead, the annular sealing bead defining an opening into the internal volume, and a sealing member including a shaft having a first end and a second end, and an engagement portion connected proximate the second end, the sealing member being partially received within the internal volume and being moveable between at least a first position, wherein the engagement portion is spaced from the sealing bead, and a second position, wherein the sealing bead is compressed between the engagement portion and the body.

In another embodiment, the disclosed bladder assembly may include a body defining a bore, a bladder closely received in the bore, the bladder defining an internal volume and including an annular sealing bead, the sealing bead defining an opening into the internal volume, a plug connected to the body to enclose the bore, the plug defining a recess and a bore extending from the recess, and a sealing member including a shaft having a first end and a second end, wherein the shaft extends through the bore in the plug such that the first end extends outside of the body and the second end extends into the internal volume, and an engagement portion connected proximate the second end, the engagement portion including a ramped portion, a seat portion and a flange, the seat portion being positioned between the ramped portion and the flange, wherein the first end of the shaft is withdrawn from the body such that the sealing bead is seated on the seat portion and compressed between the seat portion and the body.

In yet another embodiment, also disclosed is a method for sealing a bladder. The bladder may define an internal volume and may include an annular sealing bead, the sealing bead may define an opening into the internal volume. The method may include the steps of (1) providing a sealing member and a body, the body defining a bore, the sealing member including a shaft having a first end and a second end, and an engagement portion connected proximate the second end; (2) inserting the sealing member into the bladder such that the engagement portion is received in the internal volume and a portion of the shaft extends from the internal volume; (3) inserting the bladder into the bore; (4) plugging the bore such that the bladder and the engagement portion of the shaft are enclosed in the bore and the first end of the shaft extends outside of the body; and (5) applying a pulling force to the first end of the shaft to at least partially withdraw the sealing member and compress the sealing bead between the body and the engagement portion.

Other embodiments of the disclosed bladder assembly and method will become apparent from the following detailed description, the accompanying drawings and the appended claims.

BRIEF DESCRIPTION OF THE DRAWINGS

FIG. 2 is a side elevational view, in section, of a portion of the body of the bladder assembly of FIG. 1;

FIG. 3 is a side elevational view, in section, of the bladder of the bladder assembly of FIG. 1;

FIG. 4 is a side elevational view, in section, of the sealing member of the bladder assembly of FIG. 1;

DETAILED DESCRIPTION

Figure 1:
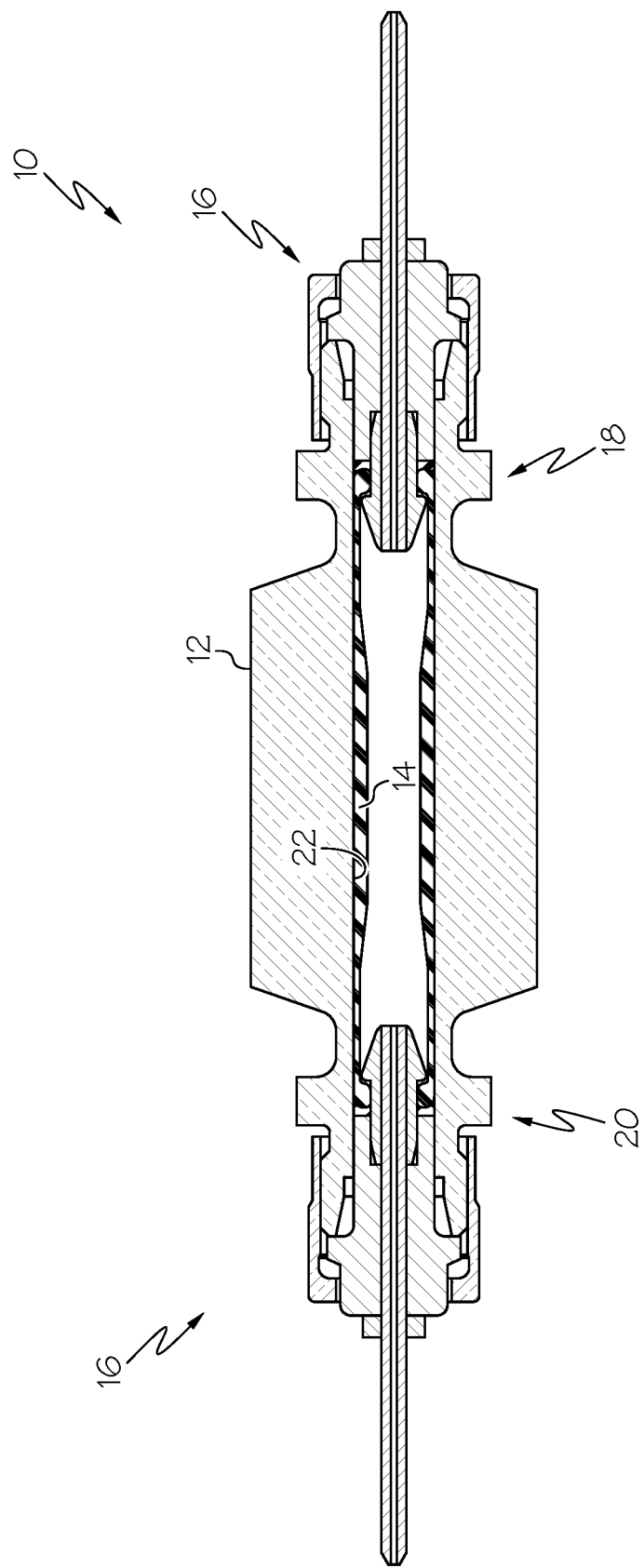
FIG. 1 is a side elevational view, in section, of one embodiment of the disclosed bladder assembly, shown in a sealed configuration.

Referring to FIG. 1, one embodiment of the disclosed bladder assembly, generally designated 10, may include a body 12, a bladder 14 and sealing assemblies 16. While the bladder assembly 10 is shown in FIG. 1 with two sealing assemblies 16 on opposed first and second ends 18, 20 of the body 12, those skilled in the art will appreciate that only one sealing assembly 16 (or three or more sealing assemblies 16) may be used depending on the application and without departing from the scope of the present disclosure.

The body 12 may be any structure capable of receiving the bladder 14, such as within a bore 22 defined by the body 12. For example, the body 12 may be an elongated tubular structure, as shown in FIG. 1. However, bodies of various shapes, geometries and sizes may be used. As one specific, non-limiting example, the body 12 may be a component of a vehicle, such as a terrestrial vehicle, a waterborne vessel or an aerospace vehicle, that may be subjected to pressurization while in use.

The body 12 may be constructed from various materials. As one non-limiting example, the body 12 may be formed from a polymeric material, such as an extruded plastic. As another non-limiting example, the body 12 may be formed from a composite material, such as a composite material having reinforcing fibers in a polymer (e.g., epoxy-based) matrix. As yet another non-limiting example, the body 12 may be formed from a metal or metal alloy, such as a high-strength aluminum alloy.

While not shown in FIG. 1, the body 12 may include various pores, cracks, holes or other through passageways in fluid communication with the bore 22, thereby rendering the bore 22 a non-fluid-tight bore. Therefore, use of the bladder 14 within the non-fluid-tight bore 22 may facilitate pressure testing of the body 12. Of course, a fluid-tight (or substantially fluid-tight) bore 22 may also be used, thereby rendering the bladder 14 a prophylactic component during pressure testing of the body 12.

The bore 22 may extend from proximate (at or near) the first end 18 of the body 12 to proximate the second end 20 of the body 12. As shown in FIG. 2, an opening 24 in the first end 18 of the body 12 may provide access to the bore 22. A similar opening may be formed in the second end 20 of the body 12 to provide access to the bore 22 at the second end 20 of the body 12.

Referring to FIG. 2, the bore 22 defined by the body 12 may have a cross-sectional profile and a maximum inner cross-sectional dimension (e.g., inner diameter) D configured to closely receive the bladder 14. For example, the bore 22 may have a generally circular cross-sectional profile. However, bores 22 having various shapes and configurations may be used without departing from the scope of the present disclosure.

Referring to FIG. 3, the bladder 14 may include a body 26 having a first end 28 and a second end 30. In one particular construction, the body 26 of the bladder 14 may be elongated along a longitudinal axis A such that the first end 28 of the body 26 is longitudinally opposed from the second end 30 of the body 26. While the bladder 14 is shown in FIG. 3 having an elongated cylindrical body 26 with a shape and configuration that closely corresponds to the shape and configuration of the bore 22 in the body 12 (e.g., the outer diameter E of the bladder 14 (unloaded) may be substantially equal to the inner diameter D of the bore 22), those skilled in the art will appreciate that the body 26 of the bladder 14 may have various shapes and configurations, depending, for example, on the shape and configuration of the bore 22 in the body 12, without departing from the scope of the present disclosure.

The body 26 of the bladder 14 may be formed from an elastomeric material, such as by molding or extruding the elastomeric materials. Various elastomeric materials and forming techniques may be used. Elastomeric material selection may include consideration of end application, such as the type of pressurizing fluid (e.g., air; water; hydraulic fluid) that may be used to pressurize the bladder. As one non-limiting example, the body 26 of the bladder 14 may be formed from natural and/or synthetic rubber. As another non-limiting example, the body 26 of the bladder 14 may be formed from silicone rubber. As yet another non-limiting example, the body 26 of the bladder 14 may be formed from a fluoropolymer elastomer material.

The body 26 of the bladder 14 may define an internal volume 32. A first opening 34 in the body 26 may provide access to the internal volume 32 proximate the first end 28 of the body 26. A second opening 36 in the body 26 may provide access to the internal volume 32 proximate the second end 30 of the body 26.

At this point, those skilled in the art will appreciated that the bladder 14 has two openings 34, 36 because the body 12 (FIG. 1) that receives the bladder 14 has two openings 24 (FIG. 2). However, bladders 14 having only one opening 34 (e.g., the second end 30 may be pre-sealed) and bladders 14 having three or more openings (e.g., a T-shaped bladder) are also contemplated.

A first sealing bead 38 may be connected to the body 26 of the bladder 14 proximate the first end 28 of the body 26. The first sealing bead 38 may be an annular structure and may protrude inward from the body 26. In one particular construction, the first sealing bead 38 may be integral with the first end 28 of the body 26 (the first sealing bead 38 and the body 26 may be formed as a single monolithic body). For example, the first sealing bead 38 may be co-molded with the first end 28 of the body 26.

A second sealing bead 40 may be connected to the body 26 of the bladder 14 proximate the second end 30 of the body 26. The second sealing bead 40 may be an annular structure and may protrude inward from the body 26. In one particular construction, the second sealing bead 40 may be integral with the second end 30 of the body 26 (the second sealing bead 40 and the body 26 may be formed as a single monolithic body). For example, the second sealing bead 40 may be co-molded with the second end 30 of the body 26.

Thus, as is described in greater detail herein, the first and second sealing beads 38, 40 may act as integral O-rings for sealing the first and second ends 28, 30, respectively, of the body 26 of the bladder 14. While the first and second sealing beads 38, 40 are shown in the drawings as having a generally circular or ellipsoidal (O-ring) cross-sectional profile, the use of other profile shapes/geometries is also contemplated.

Figure 8:
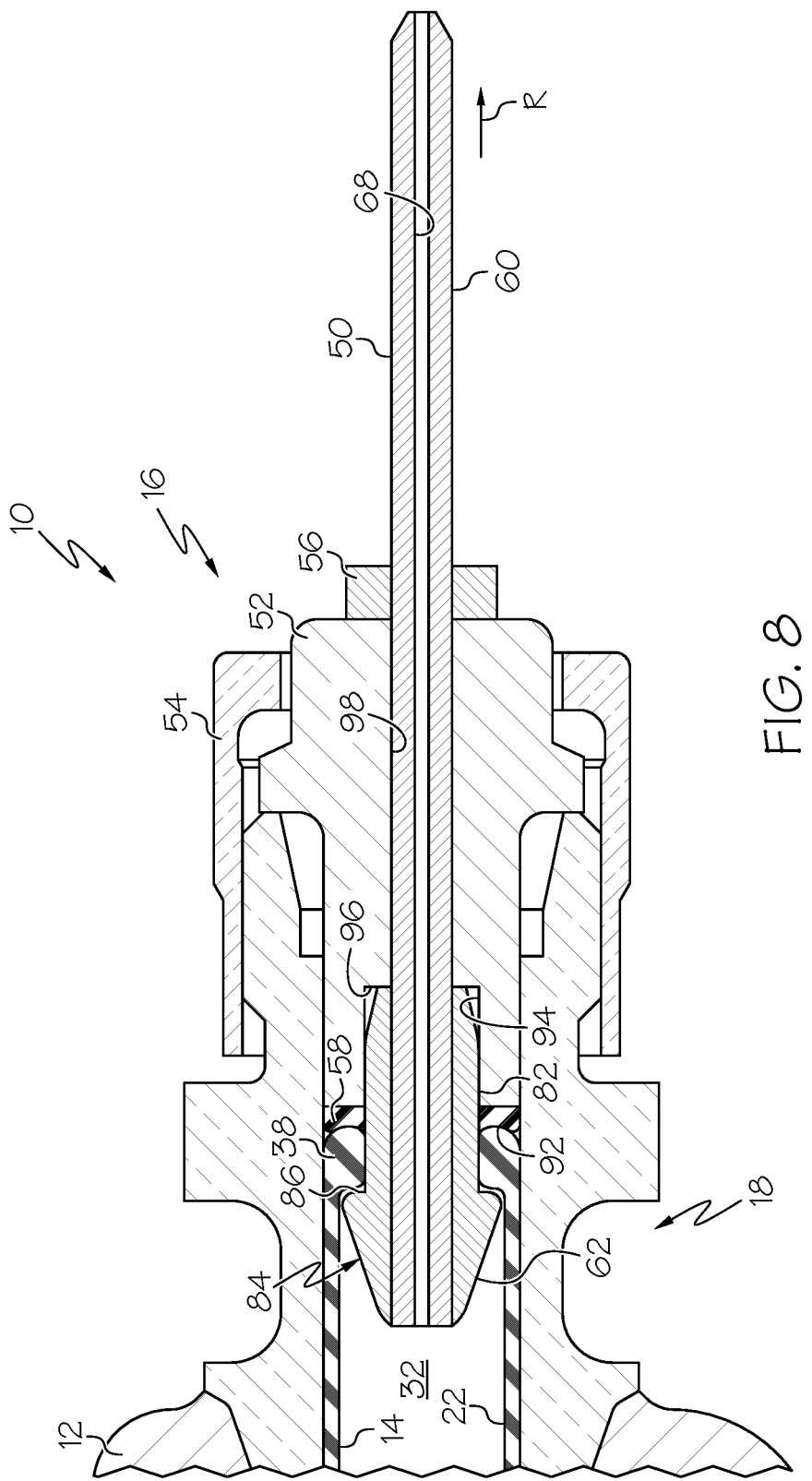
FIG. 8 is a side elevational view, in section, of the bladder assembly of FIG. 7, shown during a fourth, sealed stage of assembly.
Figure 9:
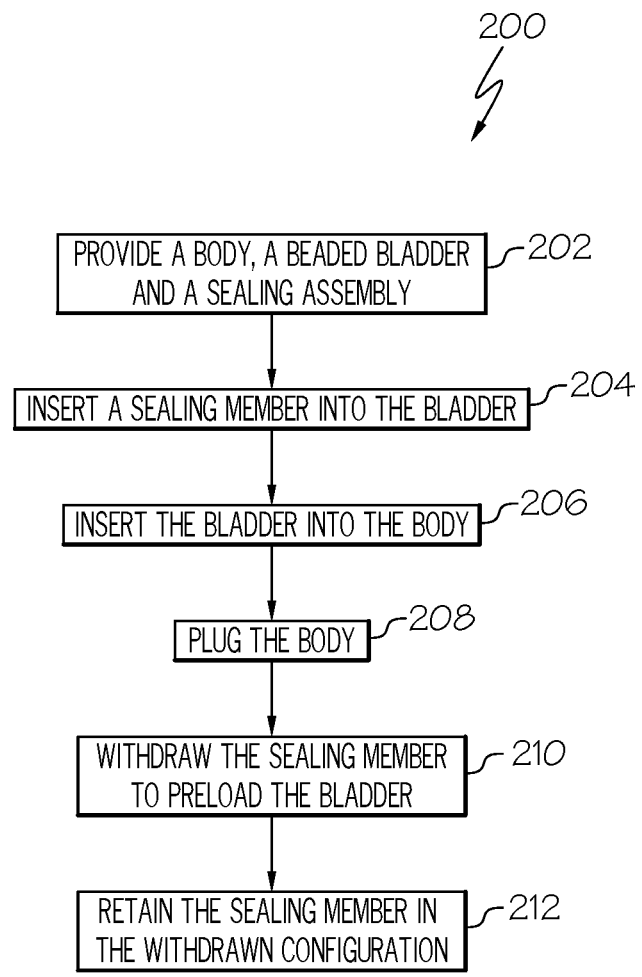
FIG. 9 is flow chart illustrating one embodiment of the disclosed method for sealing a bladder.

Referring for a moment to FIG. 8, each sealing assembly 16 (only one is shown in FIG. 8; both are shown in FIG. 1) may include a sealing member 50, a plug 52, a fastening member 54 and a retaining member 56. Optionally, such as, for example, in very high pressure applications, the sealing assembly 16 may additionally include a back-up ring 58. Additional (or fewer) components may be included in the sealing assembly 16 without departing from the scope of the present disclosure.

Referring now to FIG. 4, the sealing member 50 of each sealing assembly 16 (FIG. 1) may include a shaft 60 and an engagement portion 62. The shaft 60 may be elongated along a longitudinal axis B, and may include a first end 64 longitudinally opposed from a second end 66. The shaft 60 may optionally define a fluid channel 68 that extends from proximate the first end 64 to proximate the second end 66.

In one specific realization, the outer surface 70 of the shaft 60 may be threaded. Therefore, the retaining member 56 (FIG. 7), which may be a nut (e.g., a jam nut) or the like, may be threaded onto the shaft 60, as is described in greater detail herein. Of course, when the retaining member 56 does not require a threaded engagement with the shaft 60, the outer surface 70 of the shaft 60 need not be threaded.

The engagement portion 62 may be circumferentially received over the shaft 60 proximate the second end 66 of the shaft 60. As shown in FIG. 4, the shaft 60 and the engagement portion 62 may be separate pieces, and the engagement portion 62 may be fixedly connected to the second end 66 of the shaft 60, such as with a threaded engagement, an interference fit, mechanical fasteners, one or more welds or the like. Alternatively, the engagement portion 62 may be integral with the shaft 60 (the shaft 60 and the engagement portion 62 may be formed as a single monolithic body).

The engagement portion 62 may include a first end 72 and a second end 74 longitudinally opposed from the first end 72. The engagement portion 62 may include a ramped portion 76 proximate the first end 72 of the engagement portion 62, an optional tapered portion 78 proximate the second end 74 of the engagement portion 62, and a seat portion 80 extending between the ramped portion 76 and the tapered portion 78.

The ramped portion 76 of the engagement portion 62 may be ramped (e.g., may increase in diameter) from proximate the first end 72 of the engagement portion 62 to proximate the seat portion 80. The tapered portion 78 of the engagement portion 62 may be tapered (e.g., may decrease in diameter) from proximate the seat portion 80 to proximate the second end 74 of the engagement portion 62. The seat portion 80 may have a substantially uniform diameter extending from proximate the ramped portion 76 to proximate the tapered portion 78, which may define a first gland surface 82. The transition from the tapered portion 78 to the seat portion 80 may define a flange 84, which may define a second gland surface 86.

Referring to FIGS. 5-9, disclosed is a method 200 (FIG. 9) for sealing a bladder. The method 200 is described below with reference to FIGS. 5-8, in which only one of the sealing assemblies 16 is shown. Those skilled in the art will appreciate that the other sealing assembly 16 (shown in FIG. 1, but not shown in FIGS. 5-8) may be assembled in a manner similar to the sealing assembly 16 shown in FIGS. 5-8 to fully assemble and seal the disclosed bladder assembly 10.

The first assembly step (block 202 in FIG. 9) may include providing a body 12, a bladder 14 and a sealing assembly 16.

Figure 5:
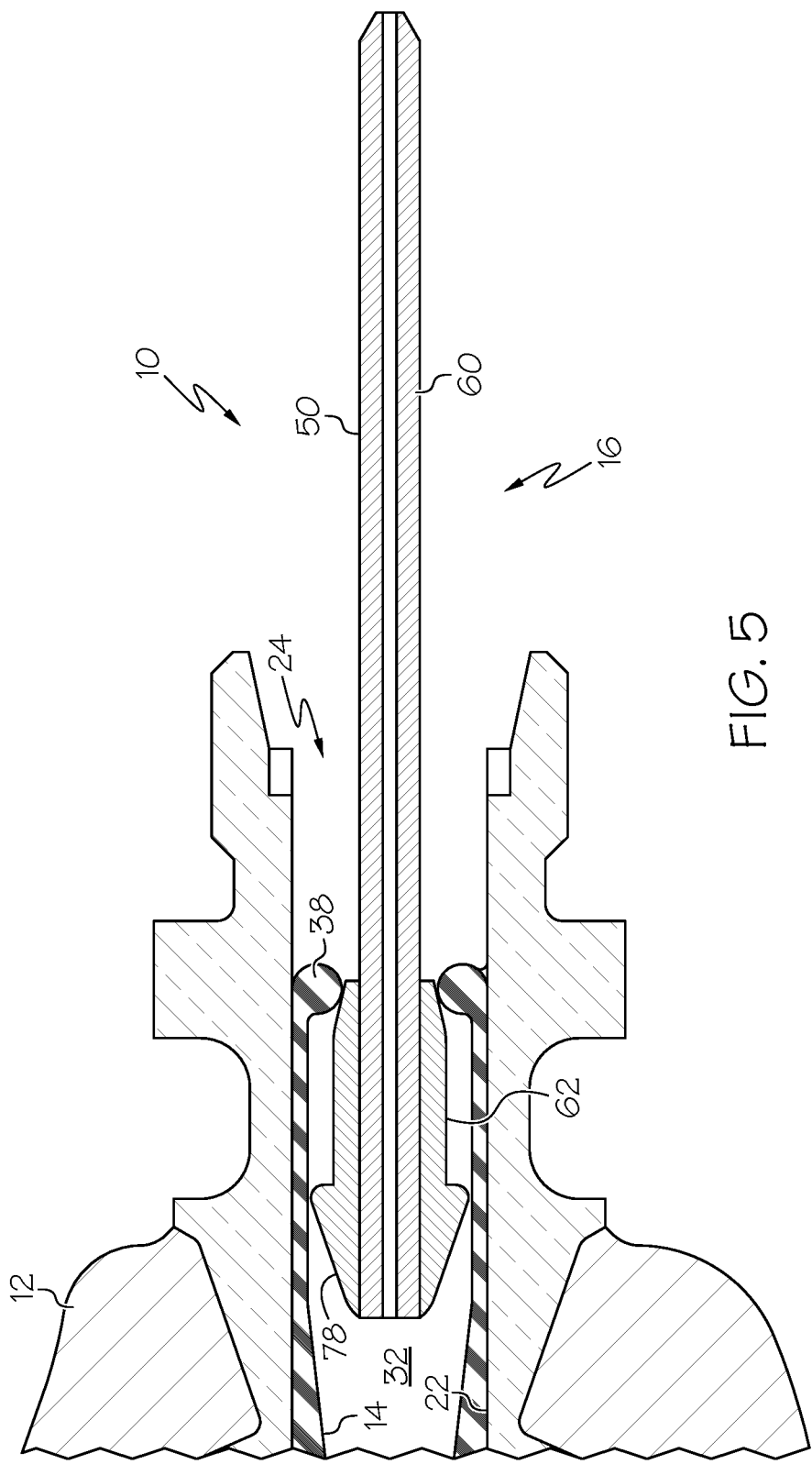
FIG. 5 is a side elevational view, in section, of the bladder assembly of FIG. 1, shown during a first stage of assembly.

The second assembly step (block 204 in FIG. 9) may include inserting the sealing member 50 into the bladder 14. As shown in FIG. 5, the engagement portion 62 of the sealing member 50 may be inserted into the internal volume 32 of the bladder 14 by way of the first opening 34 (FIG. 3) in the body 26 of the bladder 14. The tapered portion 78 of the engagement portion 62 may facilitate insertion of the sealing member 50 through the first opening 34 in the bladder 14 by urging the first sealing bead 38 outward as the tapered portion 78 is urged through the first opening 34.

The third assembly step (block 206 in FIG. 9) may include inserting the bladder 14 into the body 12. As shown in FIG. 5, an opening 24 in the body 12 may provide access to the bore 22 defined by the body 12. The bladder 14 (with the sealing member 50 inserted therein and extending therefrom) may be inserted into the bore 22 defined by the body 12 by way of the opening 24 in the body 12. When the bladder 14 is fully inserted into the body 12, the shaft 60 of the sealing member 50 may extend through the opening 24 such that a portion of the shaft 60 is outside of the body 12.

Figure 6:
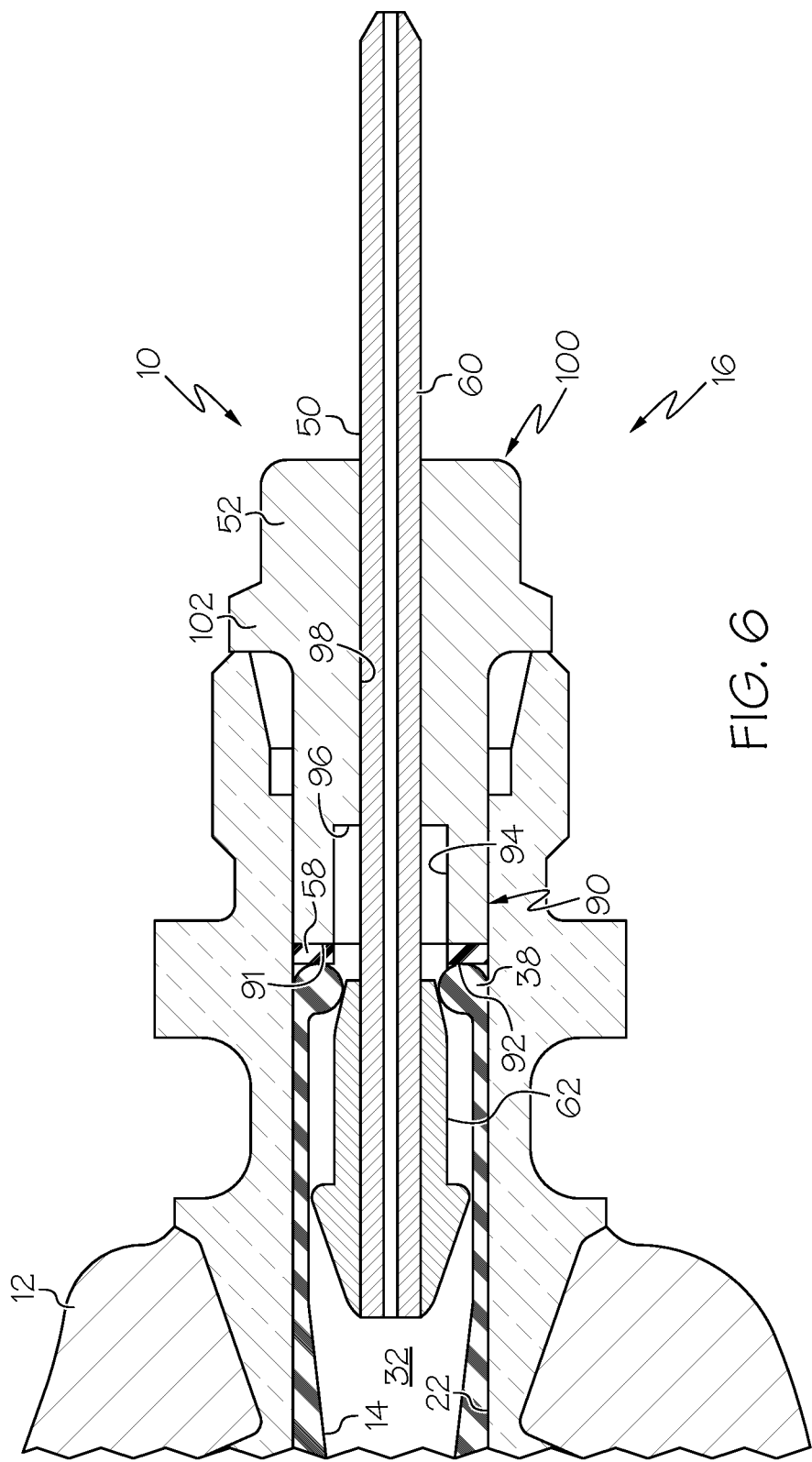
FIG. 6 is a side elevational view, in section, of the bladder assembly of FIG. 5, shown during a second stage of assembly.

The fourth assembly step (block 208 in FIG. 9) may include plugging the opening 24 in the body 12. As shown in FIG. 6, the plug 52 may be inserted into the opening 24 in the body 12 to enclose the opening 24, while permitting the shaft 50 of the sealing member 50 to extend therethrough.

The plug 52 may include a distal end 90 sized and shaped to be received through the opening 24 in the body 12 and to extend into the bore 22. The distal end 90 of the plug 52 may include a face surface 91, which may define a third gland surface. A recess 94 may be formed in the face surface 91 to receive therein a portion of the engagement portion 62 of the sealing member 50 during sealing, as is described in greater detail herein. The rear wall 96 of the recess 94 may define the depth of the recess 94 and may function as a stop for the engagement portion 62 of the sealing member 50.

The plug 52 may further define a bore 98 that may longitudinally extend from the recess 94 to the proximal end 100 of the plug 52. The bore 98 may be sized and shaped to closely receive the shaft 60 of the sealing member 50. Therefore, the shaft 60 of the sealing member 50 may extend (e.g., slidably) through the plug 52, but an interference engagement between the engagement portion 62 of the sealing member 50 and the rear wall 96 of the recess 94 may inhibit rearward movement (arrow R in FIG. 8) of the sealing member 50 beyond a pre-defined point.

Figure 7:
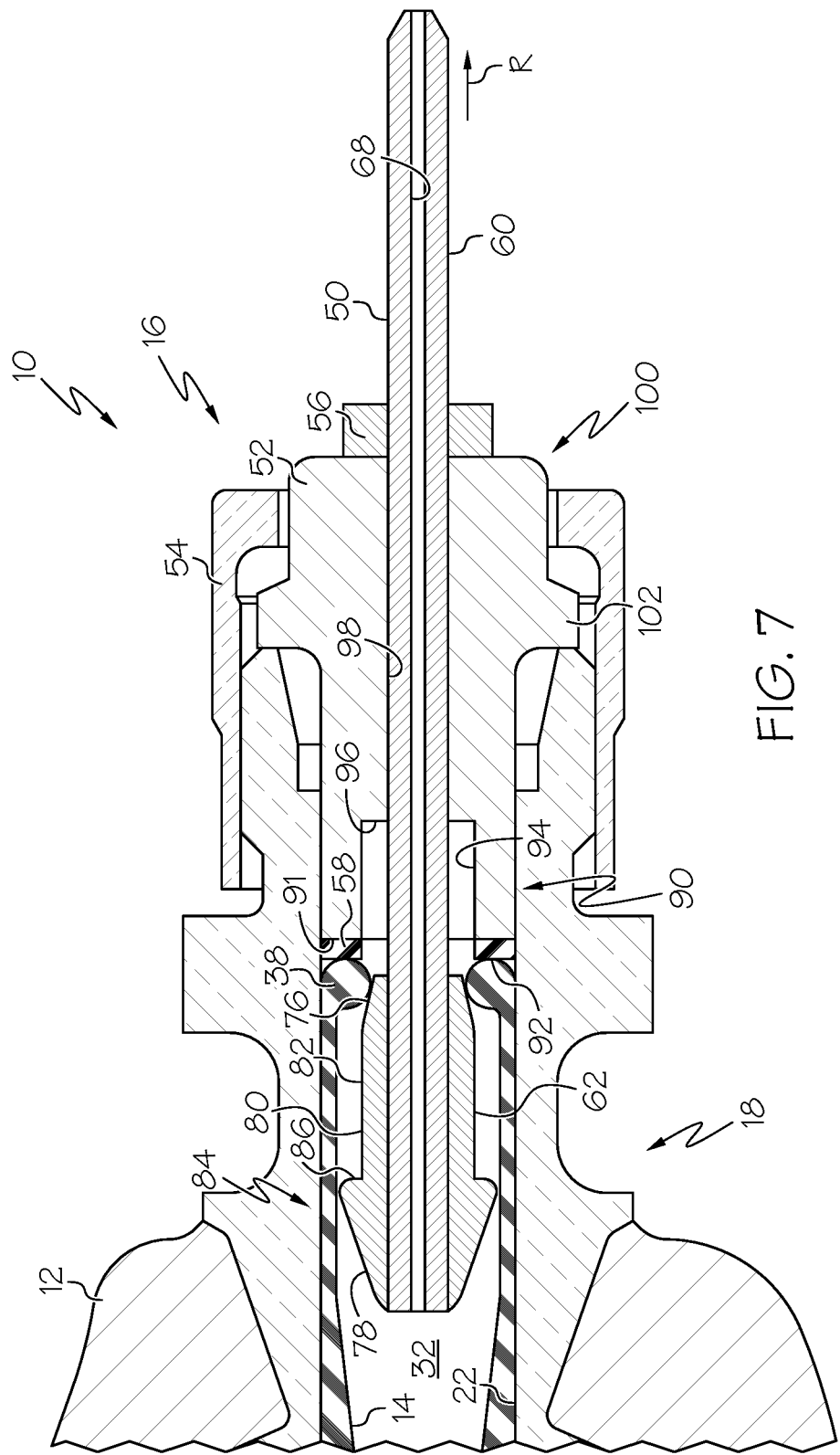
FIG. 7 is a side elevational view, in section, of the bladder assembly of FIG. 6, shown during a third stage of assembly.

The plug 52 may include an annular flange 102 to engage the body 12, thereby controlling the depth to which the distal end 90 of the plug 52 protrudes into the bore 22 of the body 12. As shown in FIG. 6, the flange 102 of the plug 52 may be in abutting engagement with the body 12. As shown in FIG. 7, the fastening member 54 may secure the plug 52 to the body 12. As one specific, non-limiting example, the fastening member 54 may be a C-nut or the like, and may be received over the proximal end 100 of the plug 52 and threaded into engagement with the body 12, as shown in FIG. 7. However, various fastening members, such as bolts, screws, pins or the like, may be used to secure the plug 52 to the body 12 without departing from the scope of the present disclosure.

In one optional implementation, the back-up ring 58 may be inserted prior to inserting the plug 52. The back-up ring 58 may be positioned against the sealing bead 38 of the bladder 14 and may be urged against the sealing bead 38 by the face surface 91 of the plug 52. Therefore, rather than the face surface 91 of the plug 52 acting as the third gland surface, the back-up ring 58 may act as the third gland surface 92, as shown in FIG. 7.

The fifth assembly step (block 210 in FIG. 9) may include withdrawing the sealing member 50 from the body 12 by applying a pulling force (arrow R in FIG. 8) to the shaft 60 of the sealing member 50 to move the engagement portion 62 of the sealing member 50 from a first position (engagement portion 62 not engaged with the sealing bead 38) to a second position (engagement portion 62 engaged with the sealing bead 38). Therefore, the step of withdrawing the sealing member 50 from the body 12 may pre-load the bladder 14.

Various techniques may be used to withdraw the sealing member 50 from the body 12. As one example, the sealing member 50 may be manually withdrawn, such as by gripping the shaft 60 of the sealing member 50 and applying a pulling force (arrow R). As another example, the sealing member 50 may be withdrawn by threading the retaining member 56 onto the shaft 60 of the sealing member 50 and tightening the retaining member 56 against the plug 52 to urge the shaft in the direction shown by arrow R. Other techniques may also be used without departing from the scope of the present disclosure.

Referring to FIGS. 7 and 8, as the sealing member 50 is withdrawn (arrow R) from the body 12, the engagement portion 62 of the sealing member 50 may engage and compress the sealing bead 38 of the bladder 14. Initially, the ramped portion 76 may compress the sealing bead 38. As the sealing member 50 is further withdrawn, the sealing bead 38 may become seated on the seat portion 80 of the sealing member 50 and, therefore, may be radially compressed between the seat portion 80 and the body 12. As the sealing member 50 is still further withdrawn, the sealing bead 38 may become axially compressed between the back-up ring 58 and the flange 84 of the engagement portion 62 of the sealing member 50. Eventually, the engagement portion 62 of the sealing member 50 may come into abutting engagement with the rear wall 96 of the recess 94 in the plug 52, as shown in FIG. 8, thereby inhibiting further withdrawal of the sealing member 50.

Thus, when the sealing member 50 is fully withdrawn, a gland may be defined by the first, second and third gland surfaces 82, 86, 92, which may be defined, respectively, by the seat portion 80 of the engagement portion 62 of the sealing member 50, the flange 84 of the engagement portion 62 of the sealing member 50, and the back-up ring 58 (or the face surface 91 of the plug 52).

The sixth assembly step (block 212 in FIG. 9) may include retaining the sealing member 50 in the withdrawn configuration. As shown in FIG. 8, the retaining member 56 may be a nut, such as a jam nut, and may be threaded onto the shaft 60 of the sealing member 50 and tightened against the plug 52 to retain the shaft 60 in the withdrawn configuration. However, use of other retaining members and retaining techniques is also contemplated. As one alternative, the retaining member 56 may be a pin engaged with the shaft 60 of the sealing member 50. As another alternative, the retaining member 56 may be a clamp secured to the shaft 60 of the sealing member 50.

Accordingly, disclosed is a system and method for sealing a bladder 14 within a body 12. Once sealed (pre-loaded), the bladder 14 may be pressurized, such as by introducing a fluid (e.g., pressurized air or hydraulic fluid) to the internal volume 32 of the bladder 14 by way of the fluid channel 68 (FIG. 4) defined by the shaft 60 of the sealing member 50.

Figure 10:
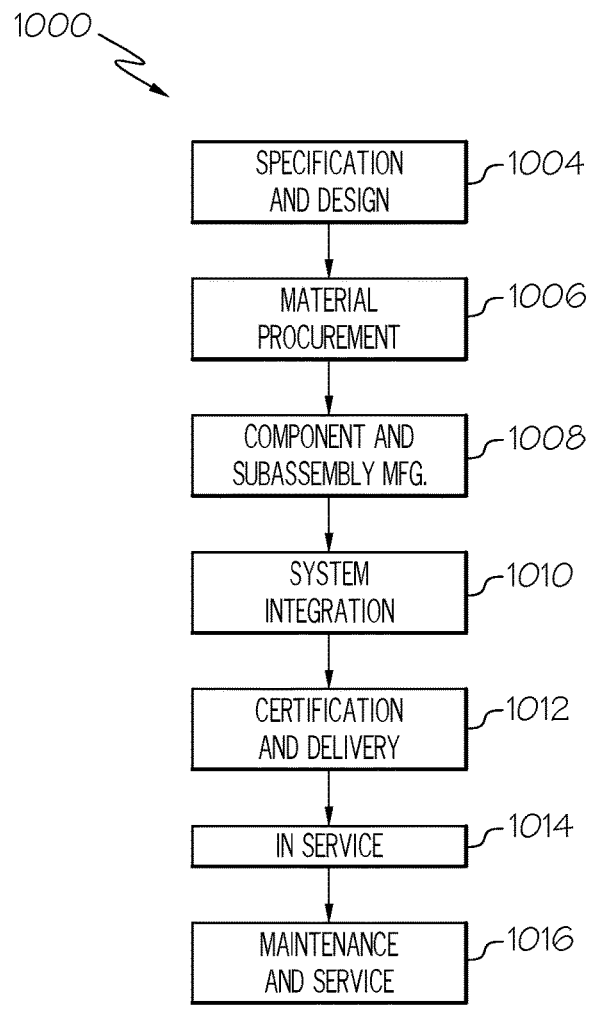
FIG. 10 is a flow diagram of aircraft production and service methodology.
Figure 11:
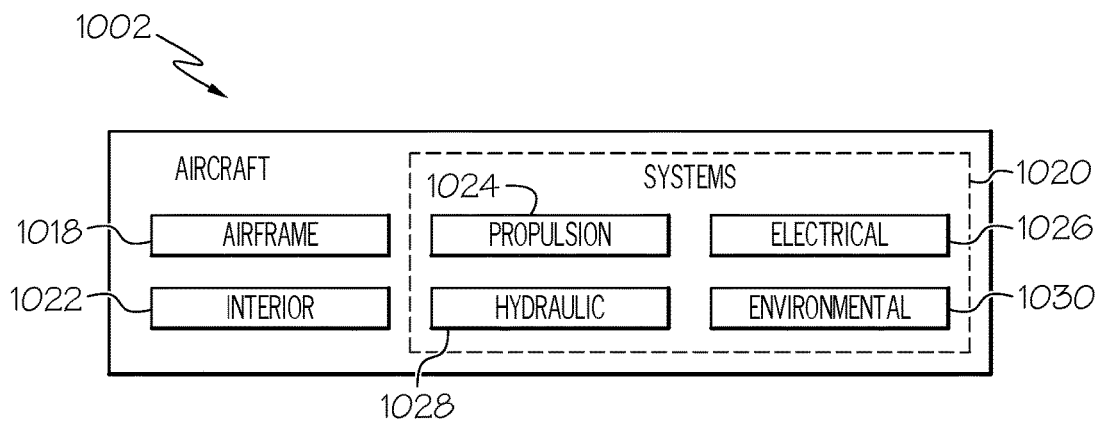
FIG. 11 is a block diagram of an aircraft.

Examples of the disclosure may be described in the context of an aircraft manufacturing and service method 1000, as shown in FIG. 10, and an aircraft 1002, as shown in FIG. 11. During pre-production, example method 1000 may include specification and design 1004 of the aircraft 1002 and material procurement 1006. During production, component and subassembly manufacturing 1008 and system integration 1010 of the aircraft 1002 takes place. Thereafter, the aircraft 1002 may go through certification and delivery 1012 in order to be placed in service 1014. While in service by a customer, the aircraft 1002 is scheduled for routine maintenance and service 1016, which may also include modification, reconfiguration, refurbishment and the like.

Each of the processes of method 1000 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 11, the aircraft 1002 produced by example method 1000 may include an airframe 1018 with a plurality of systems 1020 and an interior 1022. Examples of high-level systems 1020 include one or more of a propulsion system 1024, an electrical system 1026, a hydraulic system 1028, and an environmental system 1030. Any number of other systems may be included. Although an aerospace example is shown, the principles of the invention may be applied to other industries, such as the automotive industry.

Apparatus and methods embodied herein may be employed during any one or more of the stages of the production and service method 1000. For example, components or subassemblies corresponding to production process 1008 may be fabricated or manufactured in a manner similar to components or subassemblies produced while the aircraft 1002 is in service. Also, one or more apparatus examples, method examples, or a combination thereof may be utilized during the production stages 1008 and 1010, for example, by substantially expediting assembly of or reducing the cost of an aircraft 1002. Similarly, one or more of apparatus examples, method examples, or a combination thereof may be utilized while the aircraft 1002 is in service, for example and without limitation, to maintenance and service 1016.

Although various embodiments of the disclosed bladder assembly and method have been shown and described, modifications may occur to those skilled in the art upon reading the specification. The present application includes such modifications and is limited only by the scope of the claims.

What is claimed is:

1. A method for sealing a bladder received in a bore defined in a body, said bladder defining an internal volume and comprising an annular sealing bead, said sealing bead defining an opening into said internal volume, said method comprising:
    inserting a sealing member into said bladder, said sealing member comprising a shaft having a shaft diameter, a first end, and a second end, and an engagement portion having an engagement portion diameter that is substantially greater than said shaft diameter, said engagement portion being connected proximate said second end of said shaft, wherein said sealing member is inserted into said bladder such that said engagement portion is received in said internal volume and a portion of said shaft extends from said internal volume;
    plugging said bore such that said bladder and said engagement portion are enclosed in said bore and said first end of said shaft extends outside of said body; and
    applying a pulling force to said shaft to at least partially withdraw said sealing member and position said engagement portion within said opening defined by said sealing bead, thereby compressing said sealing bead between said body and said engagement portion.

2. The method of claim 1 further comprising the step of retaining said sealing member in said withdrawn configuration.

3. The method of claim 2 wherein said retaining said sealing member in said withdrawn configuration comprises engaging said shaft with a retaining member.

4. The method of claim 3 wherein said engaging said shaft with a retaining member comprises a threaded engagement.

5. The method of claim 3 wherein said retaining member is a nut, and wherein said engaging said shaft with a retaining member comprises threading said nut onto said shaft.

6. The method of claim 1 wherein said bore is sized to closely receive said bladder.

7. The method of claim 1 wherein said bladder comprises an elongated body having a first end and an opposed second end.

8. The method of claim 7 wherein said sealing bead is integral with said elongated body.

9. The method of claim 7 wherein said sealing bead is positioned proximate said first end of said elongated body.

10. The method of claim 1 wherein said bladder comprises an elastomeric material.

11. The method of claim 1 wherein said sealing bead protrudes inward.

12. The method of claim 1 wherein said sealing bead is radially compressed by said engagement portion when said sealing member is in said withdrawn configuration.

13. The method of claim 1 wherein said sealing bead is both axially and radially compressed by said engagement portion when said sealing member is in said withdrawn configuration.

14. The method of claim 1 wherein said engagement portion comprises a ramped portion, a flange and a seat portion.

15. The method of claim 14 wherein said engagement portion further comprises a tapered portion, and wherein said seat portion is positioned between said tapered portion and said ramped portion.

16. The method of claim 14 wherein said seat portion has a seat portion diameter and is positioned between said ramped portion and said flange.

17. The method of claim 1 further comprising connecting a plug to said body such that said shaft extends through said plug.

18. The method of claim 17 further comprising positioning a back-up ring between said sealing bead and said plug.

19. A method for sealing a bladder, said bladder defining an internal volume and comprising an annular sealing bead, said sealing bead defining an opening into said internal volume, said method comprising:
providing a sealing member and a body, said body defining a bore, said sealing member comprising a shaft having a first end and a second end, and an engagement portion connected proximate said second end, wherein said engagement portion comprises a ramped portion, a flange and a seat portion, wherein said seat portion has a seat portion diameter and is positioned between said ramped portion and said flange, and wherein said ramped portion has a minimum diameter and a maximum diameter, and wherein said seat portion diameter is at least as great as said maximum diameter;
inserting said sealing member into said bladder such that said engagement portion is received in said internal volume and a portion of said shaft extends from said internal volume;
inserting said bladder into said bore;
plugging said bore such that said bladder and said engagement portion are enclosed in said bore and said first end of said shaft extends outside of said body; and
applying a pulling force to said shaft to at least partially withdraw said sealing member and compress said sealing bead between said body and said engagement portion.

20. The method of claim 19 wherein, when said sealing member is in said withdrawn configuration, said sealing bead is both radially compressed between said seat portion and said body and axially compressed by said flange.

* * * * *